United States Patent [19]

Murdock

[11] 4,389,399
[45] Jun. 21, 1983

[54] THIOCARBAMOYL HETEROCYCLE-ANTHRAQUINONE DERIVATIVES

[75] Inventor: Keith C. Murdock, Pearl River, N.Y.

[73] Assignee: American Cyanamid Company, Stamford, Conn.

[21] Appl. No.: 345,700

[22] Filed: Feb. 4, 1982

[51] Int. Cl.³ .................. A61K 31/42; A61K 31/535; C07D 263/16; C07D 265/08
[52] U.S. Cl. ............................ 424/248.5; 424/272; 544/72; 548/229
[58] Field of Search ...................... 548/229; 544/72; 424/272, 248.5

[56] References Cited

U.S. PATENT DOCUMENTS 3,646,072  2/1972  James ............................. 260/380
4,197,249  4/1980  Murdock ........................ 260/380

OTHER PUBLICATIONS

Murdock, et al., J. Med. Chem., 22, 1024 (1979).
Zee-Cheng, et al., J. Med. Chem., 21, 291 (1978).

Primary Examiner—Richard Raymond
Attorney, Agent, or Firm—Mary-Ellen M. Timbers

[57] ABSTRACT

Novel 1,4-di(substituted amino)-5,8-dihydroxyanthraquinones wherein the substituents are alkyl-oxazolidin-2-thion-3-yl or alkyl tetrahydro-2H-1,3-oxazine-2-thione-3-yl groups as antitumor agents and as chelating agents are described.

15 Claims, No Drawings

THIOCARBAMOYL HETEROCYCLE-ANTHRAQUINONE DERIVATIVES

BACKGROUND OF THE INVENTION

The invention relates to 1,4-di[substituted-amino]-5,8-dihydroxyanthraquinones wherein the N substituents are oxazolidin-2-thion-3-yl alkyl or tetrahydro-2H-1,3-oxazine-2-thione-3-yl alkyl groups. The compounds are antitumor agents active against leukemia and melanoma.

Research for antineoplastic agents for the suppression of malignant cell growth has been and remains an area of intense interest. Several agents have been developed which inhibit growth of cancerous tumors. These include such agents as methotrexate and 5-fluorouracil. Additional agents include those described in U.S. Pat. No. 4,197,249.

SUMMARY OF THE INVENTION

The present invention is directed to 1,4-di[substituted amino]-5,8-dihydroxyanthraquinones. These anthraquinone derivatives have generic formula I

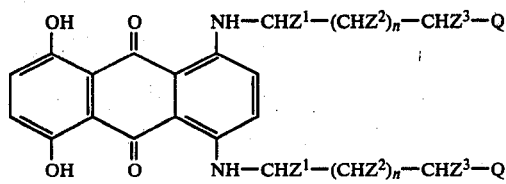

wherein

Q is 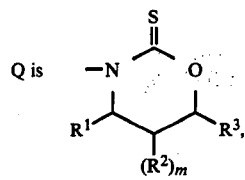

$R^1$, $R^2$ and $R^3$ are each independently selected from hydrogen or alkyl of 1 to 3 carbons; $Z^1$, $Z^2$ and $Z^3$ are each independently selected from alkyl of 1 to 2 carbons or hydrogen; n is 0 or 1; and m is 0 or 1.

The invention is directed as well to a pharmaceutical composition useful for controlling tumor growth and a method for inducing regression and/or palliation of leukemia cell growth or inhibiting growth of solid tumors, which employ an anthraquinone derivative of formula I. The pharmaceutical composition comprises an effective amount of a derivative in combination with a pharmaceutical carrier. The method for inducing regression or inhibition comprises administering by injection an effective amount of a derivative of formula I. For the composition and method, a preferred effective amount is about 3 mg to about 1.2 g per square meter of body surface area of the patient to be treated.

Preferred anthraquinone derivatives of formula I include those wherein $R^1$, $R^2$ and $R^3$ independently are hydrogen or alkyl of 1 to 2 carbon atoms, those wherein m is 0, those wherein $Z^1$, $Z^2$ and $Z^3$ are hydrogen, those wherein $R^1$, $R^2$ and $R^3$ are hydrogen and those wherein n is 0.

Especially preferred derivatives of formula I include those wherein (a) $Z^1$, $Z^3$, $R^1$ and $R^3$ are all hydrogen and m and n are 0;

(b) $R^1$ is methyl, $Z^1$, $Z^2$, $Z^3$ and $R^3$ are all hydrogen and m and n are 0; and (c) $Z^1$, $Z^3$, $R^1$, $R^2$ and $R^3$ are all hydrogen, m is 1 and n is 0.

DETAILED DESCRIPTION OF THE INVENTION

The novel derivatives of the present invention may be readily prepared by the following reaction scheme:

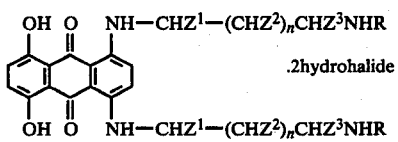

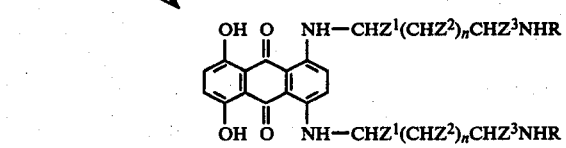

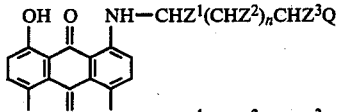

wherein R is $-CHR^1(CHR^2)_m CHR^3 OH$ and wherein n, m, Q, $Z^1$, $Z^2$, $Z^3$, $R^1$, $R^2$ and $R^3$ have the foregoing definitions.

In accordance with the above reaction scheme, a 1,4-dihydroxy-5,8-bis[w-(hydroxyalkylamino)alkylamino]anthraquinone dihydrohalide III, the preparation for which is described infra, in a polar organic solvent such as methanol, ethanol, dimethylformamide and the like is cooled and saturated with a nitrogen base such as ammonia to yield the corresponding free base II.

The free base is then converted to an anthraquinone derivative of formula I by reaction with a thioacylating agent such as carbon disulfide, dialkyl trithiocarbonate having 1 to 3 carbons in each alkyl group, thiophosgene, dialkylthiocarbonate having 1 to 3 carbons in each alkyl group, or 1,1-thiocarbonyldiimidazole. For example, the thiocarbonyldiimidazole reaction may be conducted as follows. A stirring suspension of the free base in dry pyridine, a mixture of excess pyridine and chloroform or a similar mixture of an aromatic amine base in an inert organic solvent is cooled, e.g., in an ice bath, and 2 equivalents of 1,1-thiocarbonyldiimidazole is added thereto. The reaction mixture can be stirred for from 15 minutes to 2 hours, preferably one hour longer without further cooling, then may be stirred and heated at reflux until the reaction is substantially complete, typically 1-4 hours, preferably 2 hours. The mixture is cooled. The resulting precipitate is collected by filtration and washed with pyridine, then ethanol, to yield the desired anthraquinone derivative. The other examples of the thioacylating agent can be employed in a similar manner to produce the anthraquinone derivatives of the invention.

The derivatives can be further purified by recrystallization from or leaching with lower alkanols.

The starting anthraquinone dihydrohalide of formula III is prepared according to the methods described in U.S. Pat. No. 4,197,249, which is incorporated herein by reference. In general, leuco 1,4,5,8-tetrahydroxyanthraquinone is condensed with at least 2 equivalents of an N-(w-hydroxyalkyl)alkylene diamine of the formula $NH_2CHZ^1(CHZ^2)CHZ^3R$, wherein $Z^1$, $Z^2$, $Z^3$, R and n are defined as given supra, in a polar, protic or aprotic solvent such as alkanol, water, dimethylformamide, $N,N,N^1,N^1$-tetramethylethylenediamine or mixtures thereof. The condensation is typically conducted under a nitrogen atmosphere at a temperature of from about ambient to about 100° C., preferably 40°–60° C. for about 30 minutes to 24 hours, preferably 3–6 hours to produce a leuco base of formula A:

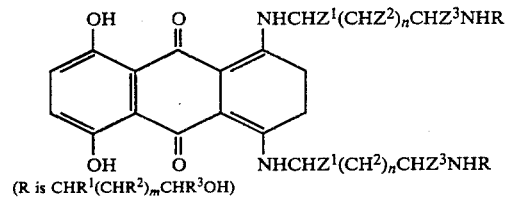

(R is $CHR^1(CHR^2)_mCHR^3OH$)

The leuco base of formula A is then converted to the aromatic free base of formula II by oxidative methods known to those skilled in the art. These methods include air oxidation by bubbling air through a solution of A, oxidation with hot nitrobenzene, oxidation in solution with about an equivalent of chloranil, hydrogen peroxide or sodium perborate. The dihydrohalide salt of formula III is prepared from the free base of formula II by adding about an equivalent or somewhat more of hydrogen halide to a solution of free base in an alkanol solvent. The salt is precipitated by addition of a nonpolar solvent such as ether, chloroform and the like. Maintaining the starting material in the salt form is desirable since it can be readily repurified and has a crystalline character.

The novel derivatives of the present invention possess the property of inhibiting the growth of transplanted mouse tumors in mice as established by the following tests.

LYMPHOCYTIC LEUKEMIA P388 TEST

The animals used were DBA/2 mice all of one sex, weighing a minimum of 17 g and all within a 3 g weight range. There were 5 or 6 animals per test group. The tumor transplant was accomplished by intraperitoneal injection of 0.5 ml of dilute ascitic fluid containing $10^6$ cells of lymphocytic leukemia P388. Various doses of the test derivatives, as indicated in Table 1, were administered intraperitoneally on days 1, 5 and 9 (relative to tumor inoculation). The animals were weighed and survivors were recorded on a regular basis for 30 days. The median survival time and the ratio of survival time for treated (T)/control (C) animals were calculated. The positive control compound was 5-fluorouracil given as a 60 mg/kg injection. The results of this test with an anthraquinone derivative of the present invention are summarized in Table I. The criterion for efficacy is $T/C \times 100 \geq 125\%$.

TABLE I

| Lymphocytic Leukemia P388 Test | | | | |
|---|---|---|---|---|
| Compound | Dose (mg./kg.) | Median Survival Time (Days) | T/C × 100 (percent) | "Cures"* |
| 1,4-Dihydroxy-5,8-bis[[2-(2-thioxooxazolidin-3-yl)-ethyl]amino]anthraquinone | 200 | 26.5 | 230 | 2/6 |
| | 100 | 24.0 | 209 | |
| | 50 | 23.0 | 200 | |
| | 25 | 25.0 | 217 | |
| | 12.5 | 22.5 | 196 | |
| | 6.25 | 21.0 | 183 | |
| | 3.12 | 19.0 | 165 | |
| | 1.56 | 16.0 | 139 | |
| | 0.78 | 16.0 | 139 | |
| Control | — | 11.5 | — | |
| 5-Fluorouracil | 60 | 18.5 | 161 | |

*"Cures" = number of survivors/total at 60 days

MELANOTIC MELANOMA B16

The animals used were $BDF_1$ mice, all of the same sex, weighing a minimum of 17 g and all within a 3 g weight range. There were normally 10 animals per test group. A one gram portion of melanotic melanoma B16 tumor was homogenized in 10 ml of cold balanced salt solution and a 0.5 ml aliquot of the homogenate was implanted intraperitoneally into each of the test mice. Various doses of the test derivative, as indicated in Table II, were administered intraperitoneally on days 1 through 9 (relative to tumor inoculation). The animals were weighed and survivors were recorded on a regular basis for 60 days. The median survival time and the ratio of survival time for treated (T)/control (C) animals were calculated. The positive control compound was 5-fluorouracil given as a 20 mg/kg injection. The results of this test with an anthraquinone derivative of the present invention are summarized in Table II. The criterion for efficacy is $T/C \times 100 \geq 125\%$.

TABLE II

| Melanotic Melanoma B16 Test | | | |
|---|---|---|---|
| Compound | Dose (mg./kg.) | Median Survival Time (Days) | T/C × 100 (percent) |
| 1,4-Dihydroxy-5,8-bis[[2-(2-thioxooazolidin-3-yl)-ethyl]amino]anthraquinone | 50 | 27.0 | 193 |
| | 25 | 25.0 | 179 |
| | 12.5 | 28.5 | 204 |
| | 6.2 | 23.5 | 168 |
| | 3.1 | 19.0 | 136 |
| | 1.5 | 19.5 | 139 |
| Control | — | 14.0 | |

TABLE II-continued

Melanotic Melanoma B16 Test

| Compound | Dose (mg./kg.) | Median Survival Time (Days) | T/C × 100 (percent) |
|---|---|---|---|
| 5-Fluorouracil | 20.0 | 25.5 | 182 |

The novel derivatives of the present invention can inhibit tumor growth such as is produced in the transplanted mouse tumor test and can induce regression and/or palliation of leukemia and related cancers in patients when administered in amounts ranging from about 3 mg to about 1.2 g per square meter of body surface per day. [The interrelationship of dosages for animals of various sizes and species and humans (based on mg/m$^2$ of surface area) is described by Freireich, E. J., et. al., Quantitative Comparison of Toxicity of Anticancer Agents in Mouse, Rat, Hamster, Dog, Monkey and Man. *Cancer Chemother Rep*, 50 No. 4, 219–244, (1966).] The course of treatment and dosage regimen for a patient will be determined by his unique condition and the judgment of his physician. In general, however, a typical dosage regimen for good results would be from about 3 mg to about 150 mg/m$^2$/day. The dosage units employed will total from about 5.4 mg to about 270 mg of the derivative for a sublect of about 70 kg of body weight when administered over a 24 hour period. This dosage regimen would be adjusted according to the physician's judgment to provide a favorable therapeutic response. For example, several divided doses may be administered daily or the dose may be proportionally reduced as indicated by the exigencies of the therapeutic situation.

The active derivatives may be administered by intravenous, intramuscular, intraperitoneal, parenteral or subcutaneous routes. Solutions or dispersions of the active derivative can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. They should be sterile and fluid enough so that they can be injected with a syringe. They should be stable under the conditions of manufacture and storage and should be preserved against the contaminating action of micro-organisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of micro-organisms can be brought about by various antibacterial and antifungal agents, for example, parabens, chlorobutanol, phenol, sorbic acid, thimerosal, and the like. In many cases it will be preferable to include isotonic agents, for example, sugars or sodium chloride. Prolonged absorption of the injectable compositions can be brought about by the use in the compositions of agents delaying absorption, for example aluminum monostearate and gelatin.

Sterile injectable solutions are prepared by incorporating the active derivative in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and other required ingredients from those enumerated above. In the case of sterile powders for the preparation of sterile injectable solutions, the preferred methods of preparation are vacuum drying and the freeze-drying techniques which yield a powder of the active derivative plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active derivative, its use in the pharmaceutical compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active derivative calculated to produce the desired pharmaceutical carrier. The specifications for the novel dosage unit forms of the invention are dictated by and directly dependent on (a) the unique characteristics of the active derivative and the particular therapeutic effect to be achieved, and (b) the limitations inherent in the art of compounding such an active derivative for the treatment of disease in living subjects having a diseased condition in which bodily health is impaired as herein disclosed in detail.

The active derivative is compounded for convenient and effective administration in effective amounts with a suitable pharmaceutically acceptable carrier in dosage unit form as hereinbefore disclosed. A unit dosage form can, for example, contain the principal active derivative in amounts ranging from about 0.1 to about 500 mg, with from about 10 to about 500 mg being preferred. Expressed in proportions, the active derivative is generally present in from about 10 to about 100 mg/ml of carrier. In the case of compositions containing supplementary active ingredients, the dosages are determined by reference to the usual dose and manner of administration of said ingredients.

Regression and palliation of cancers are attained, for example, using intraperitoneal administration. A single intravenous dosage or repeated daily dosages can be also administered. Daily dosages of up to about 5 or 10 days are often sufficient. It is also possible to dispense one daily dosage or one dose on alternate or less frequent days. As can be seen from the dosage regimens, the amount of active derivatives administered is a sufficient amount to aid regression and palliation of the leukemia or the like, in the absence of excessive deleterious side effects of a cytotoxic nature of the hosts harboring the cancer. As used herein, cancer disease means blood malignancies such as leukemia, as well as other solid and non-solid malignancies such as the melanocarcinomas, lung carcinomas and mammary tumors. By regression and palliation is meant arresting or retarding the growth of the tumor or other manifestation of the disease compared to the course of the disease in the absence of treatment.

The novel derivatives described herein are also useful as chelating, complexing or sequestering agents. The complexes formed with polyvalent metal ions are particularly stable. These properties render them useful for a variety of purposes wherein metal ion contamination presents a problem, e.g., as stabilizers in various organic systems such as saturated and unsaturated lubricating oils and hydrocarbons, fatty acids and waxes, wherein transition metal ion contamination accelerates oxidative deterioration and color formation. They are further useful in analyses of polyvalent metal ions which may be complexed or extracted by these materials and as metal carriers. Other uses common to sequestering agents are also apparent for these derivatives.

This invention will be described in greater detail in conjunction with the following specific examples.

EXAMPLE 1

1,4-Dihydroxy-5,8-bis[2-oxazolidin-2-thion-3-yl)-ethylamino]anthraquinone 100

(A) A mixture of 30.0 g of 1,4-bis[2-(2-hydroxyethylamino)ethylamino]-5,8-dihydroxyanthraquinone dihydrochloride (prepared according to the procedures given in Examples 14 and 24 of U.S. Pat. No. 4,197,249) and 300 ml of methanol was chilled in an ice bath in a Dewar flask. The stirring, cooled mixture was saturated with anhydrous ammonia. Then it was allowed to stand at 0° C. for one hour and anhydrous ammonia was allowed to flow continuously through it. The solid residue in the mixture was collected by filtration and washed by slurrying with five 150 ml portions of methanol saturated with ammonia gas to give 22.9 g of the free base 101, 1,4-bis[2-(2-hydroxyethylamino)ethylamino]-5,8-dihydroxyanthraquinone as blue-black micro rods, m.p. 175°–178° C.

(B) A suspension of 2.22 g (0.5 mmol) of free base 101 in 15 ml of dry pyridine was stirred at 0° C. and 1.78 g (1.0 mmol) of 1,1$^1$-thiocarbonyldiimidazole was added thereto. The reaction mixture was stirred for one hour without further cooling, then was stirred for 2 hours while heating under reflux. The mixture was cooled. The precipitate was collected and washed with pyridine and then with ethanol to yield 2.33 g of the above-identified anthraquinone derivatives 100 as blue-black micro needles, m.p. 273°–277° C. NMR in deutro trifluoroacetic acid, significant peaks in δppm relative to tetramethyl silane: δ7.78, δ7.49, δ4.78, δ4.09. IR KBr pellet, significant peaks: 6.20, 6.38, 6.60 microns.

Elemental Analysis Cal'd for $C_{24}H_{24}H_4O_6S_2$: C-54.54, H-4.58, N-10.60; found: C-54.67, H-4.70, N-10.85.

EXAMPLE 2

1,4-Dihydroxy-5,8-bis[2-(5-methyl-2-oxazolidin-2-thion-3-yl)ethylamino]anthraquinone 200

A mixture of 6.0 g of 1,4-dihydroxy-5,8-bis[2-(2-hydroxypropylamino)ethylamino]anthraquinone dihydrochloride (prepared according to the procedure given in Example 32 of U.S. Pat. No. 4,197,249) and 60 ml of methanol may be treated with ammonia gas under the procedure of Example 1 to give the corresponding free base 201, 1,4-dihydroxy-5,8-bis[2-(2-hydroxypropylamino)ethylamino]-anthraquinone.

A suspension of 2.29 g (0.05 mmol) of free base 201 in 15 ml of dry pyridine may be stirred at 0° C. 1.78 g (1.0 mmol) of 1,1$^1$-thiocarbonyldiimidazole may be added thereto. The reaction mixture can be further processed as described in Example 1 to give the above-identified anthraquinone derivative 200.

In a similar fashion, the other derivatives of the invention may be prepared by employing the procedures outlined in Example 1 and substituting the appropriate 1,4-bis[w-(hydroxyalkylamino)alkylamino]-5,8-dihydroxyanthraquinone dihydrohalide or a substituted form thereof, as depicted by formula III for the starting material of Example 1. For example, when m is 1 and $R^1$, $R^2$ and $R^3$ are hydrogen, the derivative synthesized by employing the procedures of Example 1, will have an oxazinidin-2-thion-3-yl moiety as its Q groups (Formula I). This moiety has the following formula:

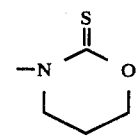

Also, in a similar fashion, the derivatives of the invention may be prepared by employing the procedures outlined in Example 1 and substituting an equivalent amount of another thioacylating agent such as thiophosgene, dialkyl trithiocarbonate, dialkylthionecarbonate or carbon disulfide for 1,1$^1$-thiocarbonyldiimidazole of Example 1.

EXAMPLE 3

Preparation of Parenteral Solution

In a solution of 700 ml of propylene glycol and 200 ml of water for injection is suspended 20.0 g of 1,4-dihydroxy-5,8-bis[2-(oxazolidin-2-thion-3-yl)ethylamino]anthraquinone 100 with stirring. The volume is made up to 1000 ml with water for injection. The formulation is sterilized, filled into 5.0 ml ampoules each containing 2.0 ml (representing 40 mg of drug) and sealed under nitrogen.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed invention are considered to be within the purview and scope of this invention and the following claims.

What is claimed is:

1. An anthraquinone derivative of the formula

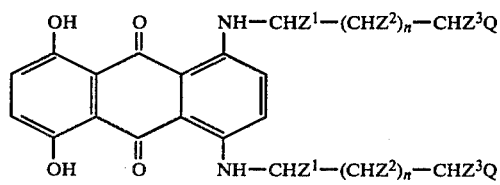

wherein:

Q is 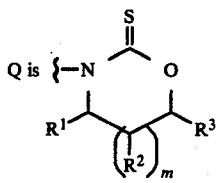

R¹, R² and R³ are each independently selected from hydrogen or alkyl of 1 to 3 carbons; $Z^1$, $Z^2$ and $Z^3$ are each independently selected from hydrogen or alkyl of 1 to 2 carbons; n is 0 or 1; and m is 0 or 1.

2. A derivative according to claim 1 wherein $R^1$, $R^2$ and $R^3$ independently are hydrogen or alkyl of 1 to 2 carbons.

3. A derivative according to claim 1 wherein $R^1$, $R^2$ and $R^3$ are H.

4. A derivative according to claim 1 wherein m is 0.

5. A derivative according to claim 1 wherein $Z^1$, $Z^2$ and $Z^3$ are all hydrogen.

6. A derivative according to claim 1 wherein n is 0.

7. The derivative according to claim 1 wherein m and n are both 0, and $Z^1$, $Z^3$, $R^1$ and $R^3$ are all hydrogen.

8. The derivative according to claim 1 wherein m and n are both 0, $R^1$ is methyl and $Z^1$, $Z^3$ and $R^3$ are all hydrogen.

9. The derivative according to claim 1 wherein m is 1, n is 0, and $R^1$, $R^2$, $R^3$, $Z^1$ and $Z^3$ are all hydrogen.

10. A pharmaceutical composition useful for inducing regression of leukemia cell growth or inhibiting growth of solid tumors in a patient, which comprises
  a pharmaceutical carrier in combination with an effective amount of an anthraquinone derivative according to claim 1.

11. A composition according to claim 10 wherein the effective amount is from about 3 mg to about 1.2 g per square meter of body surface area of the patient.

12. A composition according to claim 10 wherein the dosage amount of derivative is from 0.1 mg to 500 mg per unit of formulated combination.

13. A method of inducing regression of leukemia cell growth in a patient or inhibiting growth of solid tumors in a patient, which comprises
  administering by injection to said patient an effective amount of a derivative according to claim 1.

14. A method according to claim 13 wherein the derivative is in a pharmaceutical carrier.

15. A method according to claim 13 wherein the effective amount is from about 3 mg to about 1.2 g per square meter of body surface area of the patient.

* * * * *